United States Patent [19]

Jalinski

[11] Patent Number: 5,182,212

[45] Date of Patent: Jan. 26, 1993

[54] TIME TEMPERATURE INDICATOR WITH DISTINCT END POINT

[75] Inventor: Thomas J. Jalinski, Waunakee, Wis.

[73] Assignee: Oscar Mayer Foods Corporation, Madison, Wis.

[21] Appl. No.: 780,672

[22] Filed: Oct. 18, 1991

Related U.S. Application Data

[62] Division of Ser. No. 648,712, Jan. 31, 1991, Pat. No. 5,085,802.

[51] Int. Cl.$^5$ ............................................. G01N 31/00
[52] U.S. Cl. ................................... 436/2; 252/408.1;
252/183.11; 252/961; 252/962; 426/88;
426/232; 374/106; 116/206; 116/207; 116/216
[58] Field of Search ............... 252/408.1, 183.11, 961,
252/962; 116/216, 207, 206; 426/232, 321, 326,
88; 374/106; 436/2

[56] References Cited

U.S. PATENT DOCUMENTS

| | | | |
|---|---|---|---|
| 3,942,467 | 3/1976 | Witonsky | 116/219 |
| 4,042,336 | 8/1977 | Larsson | 422/58 |
| 4,212,153 | 7/1980 | Kydonieus et al. | 368/62 |
| 4,327,117 | 4/1982 | Lenack et al. | 426/88 |
| 4,339,207 | 7/1982 | Hot et al. | 374/160 |
| 4,362,648 | 12/1982 | Holt et al. | 252/408 |
| 4,968,522 | 11/1990 | Steinke et al. | 426/602 |
| 5,045,283 | 9/1991 | Patel | 422/56 |
| 5,085,802 | 2/1992 | Jalinski | 252/408.1 |

Primary Examiner—Richard D. Lovering
Assistant Examiner—N. Bhat
Attorney, Agent, or Firm—Lockwood, Alex, Fitzgibbon & Cummings

[57] ABSTRACT

A new and improved integrating indicator system operable to signal the attainment of one or more preselected time-temperature integrals which monitor the temperature and time history of a product utilizes a dual system of specific reaction pairs which simultaneously generate acid and alkali from two neutral substrates. One of the substrates is present in excess of the other. The preferred dynamic indicator system generates a constant pH buffer in the alkali range that is maintained until one of the substrates is depleted. At that time, a rapid pH change in the indicator solution to the acid range occurs, resulting in a very sharp visual color change in a pH-sensitive dye. In preferred embodiments, the specific reaction pairs are enzyme/substrate pairs, preferably urease/urea and yeast/triacetin. A preferred combination pH-sensitive dye package includes m-nitrophenol, p-nitrophenol and litmus to provide an indicator which changes from green to reddish pink upon the expiration of a given amount of time at constant temperature, or in a shorter period of time, upon exposure to elevated abuse temperatures. In especially preferred embodiments, one of the enzyme substrate pairs includes an enzyme component provided by a microorganism which has been shock treated prior to incorporation in the indicator to improve temperature sensitivity and provide extended half life. The new and improved integratin indicators are adapted for use with packaged foodstuffs intended for refrigerated and room temperature handling and storage at temperatures between about 20° F. to about 120° F.

6 Claims, No Drawings

TIME TEMPERATURE INDICATOR WITH DISTINCT END POINT

This application is a divisional of copending application Ser. No. 648,712, filed Jan. 31, 1991, now U.S. Pat. No. 5,085,802.

BACKGROUND OF THE INVENTION

The present invention relates to indicator systems for indicating time-temperature histories of a product. More particularly, it relates to a new and improved time-temperature integrating indicator for monitoring the safe limits of refrigerated storage for a food product or other material.

The desirability of detecting whether or not a food product has been subjected to adverse temperature conditions has been recognized and numerous indicator devices of this kind are described in the patent literature. One especially prevalent class of these indicators relates to indicators for detecting whether or not a frozen food product has been allowed to thaw. Typically, these freeze indicators include a frozen material which melts at some preselected temperature so as to irreversibly activate an indicator, either chemically or physically. Typical of these devices are those described in U.S. Pat. No. 3,437,010 and elsewhere. Most of the frozen food indicator devices merely signal a thaw, without making any attempt to measure the period during which the product is thawed or the temperature which the product attains while it is or was thawed.

Another class of known indicators for food products utilizes diffusion or capillary action with a wick or similar permeable member to provide some degree of gradation such as those shown in U.S. Pat. No. 3,414,415 and U.S. Pat. No. 3,479,877 to name but a few.

It is now recognized that various natural and synthetic materials deteriorate with the passage of time, even when taking such precautions as storing under refrigeration, packaging in an inert atmosphere, sterilization and adding spoilage retardants. For example, foods, film, pharmaceuticals, biological preparations and the like may each demonstrate decomposition with the passage of time, even when sterilized or maintained at sufficiently low temperature to preclude microbiological degradation. Decomposition may occur for various reasons including strictly chemical reactions such as oxidation and enzymatic processes. Consequently, for each type of material there often exists a limit to its permissible storage life, after which time a discernible change in some property occurs. A system which indicates when this time limit has been exceeded is desired in the food packaging industry.

The deterioration kinetics involved in these processes may be exceedingly complicated. Generally, deterioration is a function of temperature, however, the rate of deterioration of a product may vary with the temperature, so that one rate of deterioration is observed at a first temperature and a different rate of deterioration is observed at a second temperature. The overall or total amount of deterioration will depend upon the time at which the product is held at each temperature, i.e., an integral of time and temperature. The practical effects of this can be seen, for example, from two identical samples of food packaged simultaneously. For both of these there may be a finite time temperature integral until a discernible change in food quality occurs. If one package is allowed to rise in temperature by 10° or 20° or more in the course of its distribution or storage, its quality shelf life will be reduced as compared with the other package which is maintained at an appropriate lower refrigerated temperature for its entire storage life. Consumers, about to purchase these packages, both of which are now stored at a normal refrigeration display case presently have no way of ascertaining this difference in the temperature histories of the products they are buying.

Systems have been suggested for monitoring the temperature history of a product. U.S. Pat. No. 2,671,028 utilizes an enzyme such as pepsin in indicator systems. U.S. Pat. No. 3,751,382 discloses an enzymatic indicator in which urease decomposes urea with the reaction products causing a change in the pH of the system. The activity of the enzyme and thus the rate of decomposition is dependent on temperature, so that the change in pH resulting from the activity of the enzyme can be monitored by conventional acid-base indicators. Another system is described in U.S. Pat. No. 3,768,976, wherein time temperature integration is achieved by monitoring oxygen permeation through a film through the use of a redox dye.

Finally in U.S. Pat. No. 3,942,467, a time-temperature integrating indicator is described including an organic acid generating component which is subject to solvolysis at a first reaction rate to generate known amounts of acid. The solvent or solvolysis medium is provided with known quantities of alkaline materials sufficient to neutralize acid generated by solvolysis for a given time period at a given reaction temperature. The solvolytic reaction rate increases with an increase in temperature. A pH sensitive dye is provided to indicate when a sufficient amount of acid has been generated to neutralize all of the alkaline material. In a preferred embodiment, two separate alkaline materials of different basicities are employed in combination with more than one pH sensitive dye. In accordance with this preferred embodiment, the indicating solution indicates a first color until the first alkaline species has been neutralized to an extent sufficient to decrease the pH of the indicator to a first intermediate range, thereby causing a color change to a second intermediate color. The second color remains until the second alkaline material is neutralized, shifting the indicator pH into the acid range, whereupon the overall indicator changes to a third color.

In accordance with this prior art indicator, gradual changes in color are observed and time delays in generating a discernible color change may take longer than is desirable or required for certain indicator applications. Moreover, as is evident from the patent, the solvolysis of the acid precursor materials requires the use of special solvent combinations to increase the half life of the solvolytic reactions. This is undesirable in today's context, wherein the co-solvents suggested in the patent include, for example, dioxane. These co-solvents are generally to be used sparingly.

A basic problem in developing satisfactory time-temperature integrating indicators is the fact that the second derivative of time-temperature decomposition (the change in rate per unit of temperature change), differs for different products. Thus, the change in the rate of deterioration per unit of temperature change for certain fruits and berries is vastly different from the change in rate for lean meats. The values for dairy products are different from both berries and meats. Consequently, a system which is dependent on a single enzymatic reaction or the permeability of a given film would be suitable as an indicator only for those materials having a similar slope for the relationship of change of rate of decomposition of a certain kind with respect to temperature.

Time temperature integrating indicator systems are not limited in application to monitoring long storage periods at below room temperature. The same considerations apply to shorter time periods and to high temperatures. The systems can be used to ensure, for example, that products have been adequately heat sterilized. The indicator is thus admirably suited to ensure that canned goods which are autoclaved have been subjected to the appropriate time and temperature integral required to obtain a necessary degree of microorganism kill. In this case, the firing of the indicator is used as the signal that the necessary sterilizing parameters have been reached or exceeded. Similarly, indicators of this type can be used to ensure that surgical instruments have been subjected to appropriate sterilization conditions, or that pharmaceuticals have not been stored for periods in excess of that which is permissible. Similarly, indicators of this type are useful in the dairy industry to indicate that dairy products have been properly Pasteurized and the like.

A major problem with prior art time temperature integrating indicators is that their time response is generally unacceptable. Frequently, the development of sufficient color to be differentiable by the viewer, may take as long as 30 to 100% of the life of the indicator.

At present, with the advent of modified atmosphere packages and newer, safer preservative species for extending the room temperature shelf life of cooked fresh foods, the consuming public has come to enjoy a number of high quality fresh tasting food products which heretofore were unavailable. Instead of providing the food in frozen form or in a can, cooked fresh foods may be treated and stored in modified atmosphere packages and stored for sufficiently long periods under refrigerated conditions to now permit these fresher foods to be available to the consumer. Luncheon trays including a variety of luncheon meats, such as turkey and ham and cheeses are an illustrative example. The improvements making these products possible have now extended the room temperature storage stability of the products in these packages from a matter of hours to a day, to several days to a week. This permits the distribution chain for the food products to make the food products available to the consumer for immediate consumption within their improved and extended shelf life.

In theory, the ratio of the rate of change at one temperature of a property of a stored article whose deterioration is being monitored to the rate of change at a lower temperature differs for different materials. This value is often expressed for 10° increments and is represented by the symbol $Q_{10}$ for the Celsius scale and $a_{10}$ for the Fahrenheit scale. For example, within the range of 0° to −20° C. raw fatty meat and precooked fatty meat have rancidity $Q_{10}$ values of about 3, whereas, raw lean meat and precooked lean meat have rancidity $Q_{10}$ values of between 5 and 6. Vegetables generally have a spoiling $Q_{10}$ of between 7 and 8, whereas fruits and berries have a spoiling $Q_{10}$ of approximately 13. The formulation of components of any indicator system should be selected so that the change in the rate of development of signal per unit change in temperature should be compatible with the parameters desired in the article being monitored. The $Q_{10}$ value for the indicator generally should approximate the $Q_{10}$ value of a property of a given food class being measured. To make this match, the proper selection of the indicator ingredients and appropriate manipulation of the relative concentration of these ingredients needs to be performed generally in accordance with the methods described in U.S. Pat. No. 3,942,467, the teachings of which are specifically incorporated herein by reference.

Accordingly, it is an object of the present invention to provide a new and improved time temperature integrating indicator for use with food products adapted for room temperature or refrigerated storage which provides an immediate visual indication of product safety and quality.

It is another object of the present invention to provide a time temperature integrating indicator for use with foodstuffs which rapidly develops a distinct end point signal as soon as safe storage limits have been reached.

It is a further object of the present invention to provide a new and improved time temperature integrating indicator which may be used with a wide variety of foodstuffs and in a wide variety of packaging configurations.

SUMMARY OF THE INVENTION

In accordance with these and other objects, the present invention provides a new and improved time-temperature integrating indicator which comprises a first specific reaction pair including an active reagent and a substrate specific for that active reagent. The first specific reaction pair members, i.e., the active reagent and its specific substrate, are reactive to form a first reaction product. This first reaction product tends to cause the pH value of the indicator to change or be shifted in an acidic or a basic first direction away from neutrality.

The indicator also comprises a second specific reaction pair including an active reagent and a substrate specific for that active reagent. The second specific reaction pair members are also reactive to form a second reaction product. The second reaction product tends to cause the pH value of the indicator to change or be shifted in a second direction opposite the first direction and preferably beyond neutrality.

The indicator composition additionally comprises at least one pH-sensitive dye which exhibits one color for a pH in a basic pH range and a second different color for a pH in an acidic pH range.

In accordance with this invention, the substrate in the first specific reaction pair is present in a stoichiometric excess amount over the amount of substrate in the second specific reaction pair. The first reaction product and the second reaction product are reactive to form a third reaction product. The third reaction product comprises a stable pH buffer which maintains the pH of the indicator at a stable value on the second direction side of neutrality until the second reaction product is no longer produced. The second reaction product ceases to be produced in the indicator when the substrate starting material for the second specific reaction pair is depleted or is used up. When this occurs, the capacity of the pH buffer is rapidly exceeded by the first reaction product and the pH of the indicator changes very rapidly from the buffer pH value to a different pH on the first direction side of neutrality. In the process, the indicator exhibits a rapid and distinct color change from the first color to the second color or from the second color to the first color.

The sharp color change of the indicator composition is selected to occur after a predetermined amount of time has elapsed upon exposure to a relatively constant predetermined temperature or temperature range. Moreover, because the rates of the first and second specific pair reactions are temperature dependent, exposure of the indicator composition to elevated temperatures above the predetermined temperature range will cause both reactions to proceed at faster rates. Accordingly, the third reaction product will be produced at a faster rate and the substrate for the second reaction pair is depleted in a shorter time period. As a result, the buffer capacity is exceeded and the color change occurs sooner than is observed with lower temperature exposure.

The sharp and distinct color change achieved by forming a stable buffer from two temperature rate dependent but generally independent specific reactions is much quicker than prior art indicator systems which start out, not from neutral substrates as with the present invention, but rather with a highly acidic or highly basic starting solution. In these prior art indicators, a reaction product is produced which effectively neutralizes the starting solution gradually, as the reaction between reactive components in the indicator proceeds. Any color change is slow to develop due to the lag time associated with the neutralization portion of the curve.

In contradistinction, the indicator of the present invention begins with a pH-neutral substrate solution and generates a stable pH buffer having a moderate pH value on a given side of neutrality. Both the first and the second specific reactions proceed simultaneously until the second specific reaction pair substrate is depleted. At that point in time no new buffer is formed and the influence on pH of the first reaction product is generally immediately observed.

In accordance with a preferred use, the indicators of the invention are employed to indicate time-temperature histories of a product subject to biologically caused or influenced changes in product quality. A typical example includes a cooked food product intended for refrigerated storage and subject to biological degradation over time, due to the harmful effects of bacteria or fungi. The rate of deterioration in product quality for the food product will vary with respect to the duration of its storage, as well as the temperature history of the stored time period. In accordance with a preferred embodiment, the indicators of this invention employ first and second specific reaction pair components selected from biological sources and/or processes which are chosen to provide an indicator having an overall $Q_{10}$ value similar to the $Q_{10}$ value of the product being monitored.

More particularly, in accordance with a preferred embodiment, the new and improved time-temperature integrating indicator comprises a first specific reaction pair including an enzyme or enzyme active component as the active reagent and a substrate specific for the enzyme for reacting to form an acid as the first reaction product. A second specific reaction pair is also provided including a different, second enzyme or enzyme active component as the active reagent and a second different substrate specific for the second enzyme. The second reaction pair members react to form a basic second reaction product.

The indicator in accordance with this preferred embodiment includes a pH-sensitive combination dye package including a combination or mixture of m-nitrophenol, p-nitrophenol and litmus. This combination of pH dyes is effective to cause the indicator to exhibit a green color at neutral to basic pH values (>7.0) and to exhibit a distinct reddish-pink color in the acidic pH range (<7.0). The substrate for the first specific reaction pair is present in the indicator in a stoichiometric excess amount over the amount of the substrate for the second specific reaction pair. The time temperature integrating indicators in accordance with the preferred embodiment exhibit a distinct color change from green to reddish-pink after a predetermined amount of time has elapsed upon exposure to a relatively constant temperature range or, after a relatively short period of time has elapsed, upon exposure to elevated temperatures. This combination dye package is preferred herein because it employs or produces the now universal symbols of green-red to indicate go TM stop or use-do not use conditions. Other pH dyes and combinations or dyes to produce other colors and color changes may also be used if desired.

In the preferred embodiment, the second enzyme/-substrate specific reaction pair comprises a urease/urea reaction pair and the first enzyme/substrate specific reaction pair is a lipase/triacetin reaction pair. Preferably, the lipase enzyme present in the first enzyme/substrate specific reaction pair is provided in or from a microorganism source exhibiting lipase enzyme activity toward the triacetin substrate. A preferred microorganism is yeast. It has been found that microbiological sources of certain digestive enzymes may be used in the indicator systems, in accordance with the present invention, to provide a more accurate temperature responsive profile resembling the deterioration being measured over the temperature ranges of primary concern.

The harmful effect of microbial action on product quality may be monitored in accordance with this preferred embodiment of the invention by monitoring the temperature and time dependent activity of an associated artificial system containing similar microbes, as is provided in the presently preferred indicators. Expressed differently, the indicators incorporating microorganisms as reagents in accordance with this invention employ like to measure like. Moreover, the utilization of two sets of first and second enzyme/substrate specific reaction pairs results in a faster, more reactive temperature sensitivity than may be achieved in prior art indicator systems containing only one enzyme/substrate reaction pair. This is because, the enzymes and/or microorganisms exhibiting enzyme activity employed as components of the indicators have higher $Q_{10}$ values as compared with the inorganic reagents used in the above mentioned U.S. Pat. No. 3,942,467. In addition, the use of two neutral substrates together with two enzymatic reagents provides an indicator system which is a homogeneous solution which also contributes to faster indicator reaction time. If high temperature exposure of a food product exceeds a safe level, then a rapid and distinct color change for the indicator within hours, preferably within minutes or even seconds is needed or desired to indicate a spoilage condition.

In accordance with the invention, the new and improved indicator in a preferred embodiment relies on a urease enzyme/urea substrate reaction pair to measure or count out the time component of a predetermined time temperature integral. The rate of reaction for the decomposition of urea in the presence of urease to form ammonium ion and carbonate ion in aqueous medium is relatively well known over the temperature ranges expected for fresh refrigerated foods as compared to frozen foods, i.e., between about 25° F. to 110° F. For a given amount of urease enzyme, the time until conversion or depletion of the urea substrate to the ammonia and carbon dioxide end products is complete and is dependent on the reaction rate for this temperature range and the starting concentration of the urea substrate. By varying the starting concentration of urea substrate present in the indicator, the time required to deplete the urea substrate can be adjusted to establish a desired maximum time to expiration or end point for the combined integrating indicator.

The temperature monitoring component or thermal history monitoring aspect of the combined indicator is provided by the competitive, first yeast or lipase enzyme/triacetin substrate specific reaction pair of the indicator. The yeast/triacetin reaction produces one mole of glycerol and three moles of acetic acid for every mole of triacetin digested.

In accordance with the invention, the indicator may be placed in a pouch and the pouch may be affixed to a package intended to be maintained at 40° F. during storage and shipment prior to sale. As soon as the indicator components are mixed, both of its enzyme/substrate conversion reactions proceed at a first rate, respectively, determined by the 40° F. temperature. If the refrigeration breaks down, or if the product remains on a loading dock without refrigeration on a hot summer day, for example, the temperature of that product may increase several degrees for a short period of time. For every 10° F. increase in the temperature, the yeast/lipase triacetin reaction rate increases at a twelve fold rate as does the rate of the urease/urea reaction. As a result, dramatically more of the first and second reaction products are produced upon exposure to higher temperatures. The reaction products react to form a stable pH buffer until the urea substrate is depleted. Thereafter, the pH of the indicator solution drops very rapidly to the acid range. The indicator reaches its end point either, by being exposed to a constant 40° F. temperature for a given elapsed period of time or, upon exposure to elevated temperatures in a relatively accelerated or shortened period time.

In accordance with an especially preferred embodiment of this invention, it has now been surprisingly discovered that the temperature sensitivity of indicators prepared in accordance with the teachings of the present invention including a microorganism source for at least one of the enzyme-active reagents of one of the specific reaction pairs is improved by shock treating the microorganism. The preferred shock-treated indicators provide a distinct visual color change in a shorter period of time upon exposure to abuse temperatures. Moreover, the preferred shocked indicators exhibit extended shelf lives under nonstressed, refrigerated temperature storage.

In accordance with this aspect of the invention, unexpectedly improved time-temperature integrating indicators are provided by shock treating a microorganism containing indicator composition prior to assembling the indicator onto a product package. More particularly, the microorganism shock treatment is generally a process which alters or partially alters the cellular structure of the microorganisms but which does not alter or denature the subcellular structures or proteins. Spores from the treated microorganism may be used directly. Illustrative methods for disrupting or altering the cellular structure of the microorganism referred to as shock treatment herein may include heat treating, Pasteurization, sonification, radiation, chemical exposure to acid or base or a combination thereof. The shock treatment should not be so extreme so as to destroy the biospecific activity of the enzyme being contributed by the microorganism or whatever other protein structures are being subcellularly provided by the microorganism and responsible for the digestion or other reaction relied upon.

The heat-shocked microorganisms tend to respond more rapidly at abuse temperatures allowing for the use of higher urea levels on the base side of the indicator. This surprising and unexpected discovery means that a time-temperature sensitive indicator may now be provided for monitoring longer shelf life products. Without wishing to be bound by any particular theory, the improved performance of heat shocked microorganisms as compared with unshocked microorganisms may be due to the fact that the cell membranes of the microorganisms limit solution effects such as diffusion and may reduce the contact of the substrate molecules and the enzymes. In the shocked microorganism indicators, the cellular membranes of the microorganisms have been disrupted, possibly permitting release of the enzymes into solution and more complete diffusion of the substrate molecules to and from the enzymes.

The microorganism reagent route for indicators of this type is also attractive from an economic standpoint, since very small quantities of microorganisms are needed to provide satisfactory levels of enzymes. Very large numbers of microorganisms can be produced relatively inexpensively. The ability to shock the microorganisms to thereby provide altered microorganisms increases the safety of using these materials without dramatically increasing the cost. Moreover, the ability to employ untreated microorganisms to provide the required enzymes followed by shock treatment is economically attractive as compared with the cost of isolating and purifying the enzymes.

The new and improved indicators of the present invention may be placed on or in the vicinity of a product to be monitored. The integrating indicators may be associated with packaging in any one of a large number of ways. Preferably, an indicator pouch or envelope is provided from a clear film web approved for use with packages of this product. A piece of filter paper may be placed in the indicator pouch and minute quantities of the premixed indicator may be added dropwise onto the filter paper to form an indicator patch. The pouch is sealed and thereafter is placed on the package so that the patch is visually observable from the outside of the product package. The prepared indicator pouches may be stored at low temperatures, preferably at temperatures below 0° until desired for use. Thereupon, the frozen pouches may be removed from low temperature storage and affixed to the outside of the product package by means of a pressure sensitive adhesive, or other suitable attachment means.

Alternatively, the indicator system may be provided in the form of a 2-part composition which is placed in a 2-compartment barrier pouch affixed to the product packaging. The individual parts are segregated from each other by means of a rupturable film barrier which may be ruptured to mix the indicator components to start the io functioning of the indicator at an appropriate starting point. Moreover, a smaller sealed envelope or see-through pouch of packaging film material containing the indicator may be placed in an observable location within the product package or on the exterior thereof to provide a visual indication of freshness. As has been mentioned above, the indicator pouch can be affixed to the product packaging by any suitable means including by the use of adhesives and/or simple and double sided adhesive tape strips may be used. Where the packaged product is a foodstuff such as a packaged meat, it is preferred to place the indicator pouch on the outside surface of the package to monitor temperatures experienced by the product at the surface of the meat or other food product. In this manner, the indicator solution will be exposed to generally the same elevated temperatures as the outer surface of the food product, which is usually where spoilage begins on the product.

Other objects and advantages of the present invention will become apparent from the following Detailed Description of the Invention and the illustrative Examples.

DETAILED DESCRIPTION OF THE INVENTION

In accordance with a preferred embodiment, the new and improved time-temperature integrating indicator of the present invention comprises a first specific reaction pair including an active reagent and a substrate specific to said active reagent. In the preferred embodiment, the first specific reaction pair is reactive to form a first reaction product which causes or tends to cause the pH value of the indicator composition to change in an acidic first direction on the acid side of neutrality. The first specific reaction pair is for generating acid in the indicator.

By "specific reaction pair" herein is meant an observable bio-specific tendency for the active reagent and its substrate to react and form a given reaction product, regardless of the presence of other factors which normally hinder or adversely influence non-bio specific interactions such as pH (within limits), solution effects, relative concentration of reactants, the presence or absence of other materials in solution or the like. Illustrative specific pair reactions include those reactions between enzymes and their substrates, enzyme-cofactor interactions, antibody-antigen reactions, immunological reactions and other types of bio-specific interactions to name a few.

In the preferred first specific pair, the active reagent reactive with the first substrate to produce an acidic first reaction product preferably is an enzyme or a microbiological organism or entity which exhibits enzyme activity with respect to the substrate. An especially preferred first specific reaction pair includes yeast as the active reagent, alone or in combination with added lipase enzyme, and a triacetin substrate. Other acid-generating microbes which may be used herein as the first active reagent include lactobacilli which react with glucose to produce lactic acid. Other lactic acid-producing organisms which digest various sugars or carbohydrates to produce bio-acids or organic acids such as lactic acid including the lactobacilli, streptococci and pediococci, may also be employed with their respective carbohydrate substrates to provide the first specific reaction pair.

The active reagents and their specific substrates for use herein as the first specific reaction pair are generally commercially available and may be obtained from a number of sources. For example, a suitable yeast is sold under the tradename RED STAR ®. Lactobacilli may be obtained under the tradename LACTACEL ® from Microlife Technologies, Sarasota, Florida. Triacetin, a triacetic acid ester of glycerol also known as glycerol triacetate, and various glucose and carbohydrate solutions may be obtained from several commercial sources.

The second specific reaction pair in the indicator is for generating a base which changes or tends to change the pH of the indicator to the basic side of neutrality and to maintain the pH in the basic range until the second pair substrate is depleted.

The second specific reaction pair also comprises an active reagent and a second substrate with which or upon which the active reagent acts to generate a basic second reaction product. Preferably, the active reagent in the second specific reaction pair is also an enzyme or a biological organism or entity exhibiting enzyme activity towards a selected substrate for generating base. In the preferred embodiment, the second specific reaction pair is reactive to form a second reaction product including ammonia. Accordingly, enzyme-substrate pairs known to generate ammonia are preferred. Especially preferred second specific reaction pair members are urease and urea, as well as, micro-organisms exhibiting significant urease activity and a urea substrate. Other enzymes known to generate ammonia in connection with the digestion, or metabolism or catabolism of proteins, amino acids or nitrogen-containing bases might also be successfully employed. Urease is commercially available in many forms. One commercially available form is Jack bean meal powder with documented urease activity from Sigma Chemical Company. The urea substrate for the urease/urea enzyme/substrate pair is a standard chemical reagent available from a number of sources.

The amount of urease enzyme and the relative amount of urea substrate used may be varied between reasonable limits. For example, the concentration of urease enzyme provided should be high enough so that a sufficiently strong green coloration of the indicator characteristic of the pH buffer initially appears. An upper limit for the amount of urease may be determined by reaching a point of diminishing returns, namely, that adding more urease enzyme does not significantly increase the rate of production of urea decomposition products in the indicator and unnecessarily increases the expense.

The relative proportion of urea added to the indicator may change the time component of the indicator function. For a given amount of urease enzyme, for example, varying the concentration of urea added to the indicator will vary the time required to reach an end point signal in a non-temperature stressed indicator sample. For example, at a first starting concentration of urea, the indicator may not reach its color change time end point signal until two days have passed at exposure to 80° F., whereas at a higher starting concentration, the same indicator system may take 3.5 days to reach its time end point signal color change.

The new and improved time temperature integrating indicator systems of the present invention include at least one pH sensitive dye. In the preferred embodiment, a pH sensitive combination dye package including m-nitrophenol, p-nitrophenol and litmus is included for the indicator. The meta- and para-nitrophenols exhibit a yellow coloration in the basic pH ranges above 7.0 with a sharp change to colorless at 7.0 and less. The litmus dye exhibits a dark blue color in the basic pH ranges above 7.0 and a distinct reddish pink color at a pH in the acidic range below 7.0. The preferred combination of dyes therefore provide the indicator solution with a green color until such time as the urea substrate and the third reaction product pH buffer has been completely depleted and the pH of the indicator system has shifted to the acid range, whereupon a vivid and rapid reddish pink color develops. The pH sensitive dye package should provide a distinct color change near neutrality, pH=7.0 and preferably relies on an unmistakable signal value, such as a change from green to red, to indicate an expiration warning. Although the above-package is preferred, other combinations may be used, such as a combination of bromothymol blue and neutral red. If this later combination is employed, the indicator is initially green and changes to an orange red color in the acid range.

The indicator solution is preferably an aqueous solution or a mixture of all of the ingredients, and may optionally include other ingredients, such as a monosodium phosphate buffer and/or a carbohydrate energy source for the microorganism, such as, preferably glucose may be provided. The indicators may also include a water-miscible co-solvent such as, any polar organic solvent, including, for example, lower alkanols such as ethanol, liquid ketones, such as acetone or methylethylketone, to name but a few.

In accordance with the present invention, the various components of the indicator solution are immediately premixed prior to packaging with the food products. This commences the chemistry of the indicating reactions and accordingly, ammonia will be steadily produced from the second enzyme/substrate pair immediately after mixing, at a reaction rate determined by the ambient temperature. The total amount of the individual components comprising the indicator of the present invention are determined by such considerations as the manufacturing process costs, material compatibilities, application and the like and these factors are, in turn, largely determined by matters of convenience or design choice. Since the indicator system begins reacting as soon as the components are mixed or brought into contact, it is apparent that these components may be kept separated until such time as activation of the indicator is desired. Therefore, the components comprising the indicator may be enclosed in a rupturable container which is associated with a food package, or with a simple one part pouch or envelope container. In a 2-part package indicator may be provided so that one portion of a rupturable barrier package contains the enzyme and the microbes responsible for providing at least the second enzyme component an illustrative 2-part package is described in U.S. Pat. No. 3,977,945. The dyes and substrates may be placed in the other chamber of the barrier package. In use, the blister-pack is squeezed to rupture the barrier between the two parts to mix and form the indicator. The product packaging materials are preferably transparent and fabricated from chemically inert resilient materials such as polyethylene. Moreover, the packaging for the indicator pouch or pocket is preferably also made from a polyethylene film. The pouches or envelopes may be provided with an adhesive backing or may be affixed in some other manner to the food packaging.

Alternatively, it is of course possible to mix the components of the indicator together in the course of manufacture and to fill and seal a single compartment containers. In a preferred embodiment, the indicator is added onto a wetted piece of filter paper which is placed in a pocket or envelope which is adhesively bonded to the outside surface of a food container. In accordance with this single compartment approach, a reeled tape of an absorbent substrate may be un-rolled and passed through a treating station. The mixed indicator compositions may be applied to the substrate tape at this treating station to form a wetted indicator tape. The wetted tape may be rerolled onto a reel and frozen until it is ready to be cut into small pieces for insertion in a pouch envelope. The wetted tape may be cut and assembled into a pouch or strip of continuous pouches which are thereafter frozen if desired. Freezing of the indicator solution may help to prevent the reactions from occurring, or may dramatically reduce the rates of reactions, so that the indicators are effectively "on hold" or "turned off" while frozen or chilled until they are ready for use.

Other objects and advantages of the present invention will become apparent from the following working Examples as follows:

DESCRIPTION OF THE PREFERRED EMBODIMENTS

EXAMPLE 1

A new and improved time-temperature integrating indicator was prepared as follows:

A 2% cold filtered sterilized solution of urease reagent was prepared by admixing 2 grams of Jack bean meal powder with urease activity (SIGMA) Chemical Co. in 100 mls of de-ionized water to which a diatomaceous earth filter aid was added. The admixture was cold-filtered through a 0.2μ Millipore filter to provide about 100 mls of a clear, substantially bacteria-free aqueous urease solution.

Part A of the indicator was prepared by making a solution of the following:

2.0 grams of a 0.4 M $NaH_2PO_4$
6.0 grams of triacetin (glycerol triacetate)
1.0 gram of glucose
0.4 grams of urea
5.0 grams of the 2% cold filtered urease solution prepared above and
0.1 grams of dry yeast A Part B solution for the indicator composition was prepared as follows:

In a 100 ml volumetric flask containing about 50 mls of deionized water 0.01 grams of m-nitrophenol, 0.01 grams of p-nitrophenol and 0.05 grams of litmus were added and the mixture was agitated until each of the pH-sensitive dyes were completely dissolved to form a clear solution.

Thereafter 10 grams of the Part A solution were added to the Part B dye solution in the flask which turned a medium green color. 10 grams of reagent grade ethanol was also added and the combined solution in the flask was diluted with de-ionized water to 100 ml volume.

The indicator solution was incorporated into an indicator label suitable for use with food packaging by first cutting ¼ inch diameter discs from white filter paper. The paper disks were placed in envelopes or pouch pockets made from 2 ml thickness linear low density polyethylene film measuring about ½ of an inch square. Three sides of the pouch were heat seamed in a DYNO ® packaging machine. The filter paper was inserted in the interior cavity of the pouch thus formed. Thereafter, 30 μl of the green-colored indicator solution was transferred by an auto-pipettor onto the paper disk and the open top of the pouch was immediately sealed using the Dyno equipment.

The results obtained are set forth in Table 2, as follows:

TABLE 2

EFFECT OF VARYING UREA SUBSTRATE CONCENTRATION IN HEAT SHOCKED INDICATORS

| | Example: | | | | | | | | | | | | | | | |
|---|---|---|---|---|---|---|---|---|---|---|---|---|---|---|---|---|
| | 6 | B | 7 | C | 8 | D | 9 | E | 10 | F | 11 | G | 12 | H | 13 | I |
| Urea Content, % by Weight | 0.1% | 0.1% | 0.2% | 0.2% | 0.3% | 0.3% | 0.4% | 0.4% | 0.1% | 0.1% | 0.2% | 0.2% | 0.3% | 0.3% | 0.4% | 0.4% |
| Time to Endpoint, Days: | | | | | | | | | | | | | | | | |
| @ 80° F. | 0.4 | 1.04 | 1.21 | 1.83 | 1.77 | 2.34 | 2.63 | 3.34 | — | — | — | — | — | — | — | — |
| @ 40° F. | — | — | — | — | — | — | — | — | 16.50 | 16.51 | 44.01 | 42.03 | 54.90 | 42.43 | 88.00 | 67.14 |

The pouch pocket containing the indicator was transferred to a controlled temperature oven and maintained at 80° F. Under these conditions, the indicator composition of Example 1 changed from a green-colored disk to a vivid reddish-pink disk within 2.0 days.

EXAMPLE 2

Another indicator solution was prepared by the same method employed in Example 1, except that the amount of urea added to the Part A solution was increased from 0.04 grams to 0.1 grams of urea.

This indicator was placed in an indicator pouch label and tested at 80° F. in accordance with the method of Example 1. The indicator of Example 2 changed color from green to reddish pink within 3.5 days.

EXAMPLES 3-5

The following examples illustrate the improvement in performance obtained by shocking microorganisms incorporated into the indicator composition.

An aqueous solution of 0.0011% sodium phosphate, 6% triacetin, 1% glucose, 0.4% urea, 0.1% Jack Bean Meal and 0.1% yeast was diluted 1 to 10 with a solution containing 0.05% litmus, 0.01% p-nitrophenol, 0.01% m-nitrophenol and 10% reagent alcohol. Dried Yeast was used directly or mixed with water and heated in a water bath for 1 hour at 180°, 190° F. or 200° F. This was followed by chilling to 37° F.

One-half inch paper disc (Schleicher and Schnell) were dipped into the solution, placed into polyethylene pouches, frozen at −65°, vacuum sealed and stored at 80° F.

The results obtained are set forth in Table 1, as follows:

TABLE 1

EFFECTS OF HEAT-SHOCKING TREATMENT ON INDICATOR PERFORMANCE

| Example | Treatment | Days to Reach Endpoint at 80° F. |
|---|---|---|
| A | No Heat | 3.34 |
| 3 | 180° F. for 1 hour | 3.09 |
| 4 | 190° F. for 1 hour | 2.71 |
| 5 | 200° F. for 1 hour | 2.22 |

EXAMPLES 6-13

The same solution preparation method of Examples 3-5 was repeated with various amounts of urea.

The yeast for the test samples was mixed with water and heated on a steam table for ½ hour (temperatures reaching 165° F.). The indicators were held at 80° and 40° F.

Average $Q_{10}$'s (reaction rate change with every 10° C. change) of the test samples were approximately 13.5 as compared to 9.0 for the control samples.

Increasing levels of urea extends the shelf-life of the indicator at refrigerated temperatures of 40° or less. However, limited concentrations of urea are used in this system because untreated microorganisms respond slowly at abuse temperatures of 80° F. or higher to produce visual changes in the indicator. "Heat shocked" microorganisms respond more rapidly at abuse temperatures, allowing for the application of higher urea levels. Thus, a temperature sensitive indicator has been developed which produces a visual change in a shorter time at abuse temperatures and a longer time at refrigerated temperatures.

The microorganisms treatment may not be limited to "heat shock." Other examples may possibly include: pasteurization, sonification, radiation, chemical exposure, acidity, alkalinity or any combination thereof. Generally, any process which will alter or partially alter microorganisms cells (but not the spores) is considered suitable. The direct use of pure spores may be employed.

EXAMPLE 14

Another new and improved time-temperature integrating indicator was prepared as follows:

An acid free biological enzyme active reagent was prepared in the following manner: a frozen slurry sample of Pedioccocus bacteria available from Microlife Technologies, Sarasota, Fla. and sold under the trade designation LACTACEL ® 115 Was obtained. LACTACEL ® 115 is sold as a starter culture for sausage making. A 0.5 gram sample of the frozen slurry was thawed. The thawed bacterial solution had a pH of about 5.0. 2.5 ounces (about 75 mls) of thawed LACTACEL ® were placed in a flask and diluted with deionized water to 450 mls. The diluted sample was centrifuged in an International Centrifuge apparatus at a setting of 2,000 rpm for a period of 30 minutes. The supernatant water was carefully decanted. The concentrated bacterium was again diluted to 450 mls with deionized water, and was re-centrifuged. Again, the supernatant liquid was carefully decanted. The remaining bacterial residue was re-suspended in deionized water to 75 mls of volume. The washed LACTACEL ® 115 ® product had a pH of 7.0. The 75 ml washed sample was refrozen and maintained at −60° F. until ready for use.

Another indicator composition in accordance with this invention was prepared by making a 100 ml solution of the following ingredients:

5.0 mls of thawed, rinsed LACTACEL ® 115;

4.62 grams of APT broth;
5.0 grams of 2% Jack Bean meal solution (as prepared in Example 1);
5.0 grams of glucose (lactose may be substituted);
0.09 grams of urea;
0.04 grams of m-nitrophenol;
0.004 grams Neutral Red;
0.01 grams bromothymol blue.

The above ingredients were agitated briefly until a clear, green colored solution was obtained.

Indicator labels including a ¼ inch diameter filter paper disks and ½ inch square polyethylene film pouches were prepared in accordance with the method of Example 1, 30 μl of the indicator solution of Example 14 was added to each of pouches and the pouches were sealed on Dyno equipment.

One portion of the pouches were transferred to a controlled temperature oven maintained at 80° F. and another group of pouches were placed in a 40° F. refrigerator. Under these conditions, the Example 14 indicators after continuous exposure at 80° F. changed from a green colored to a reddish orange colored label after 2.0 days. The pouches maintained at 40° F. remained unchanged after at least 95 days.

EXAMPLE 15

According to this Example 1,000 lbs. of fresh turkey breast are injected with a brine solution comprising 90% water. The turkey breasts each ranged in weight from 2.5 to about 3.75 lbs. The turkey breasts are placed on a rack in an oven and cooked at a high humidity at 160° F. dry bulb for two hours and then at 170° F. dry bulb until the internal temperature of the turkey breasts is about 160° F. After cooking, the turkey breasts are removed from the oven, cut into quarters and then coated with a preservative solution. The turkey breasts were then cooled to approximately 32° F. and then vacuum packed in moisture-oxygen barrier films of ethylene vinyl acetate and saran laminated material.

An indicator label pouch is prepared in accordance with the method of Example 14 and is affixed by means of a pressure-sensitive adhesive onto the outer surface of the vacuum packaged breasts. Prior testing had revealed that when these vacuum packaged turkey breasts are carefully maintained under refrigerated storage at 40° F. or less, they have an average shelf life of about 65 days. The indicator will not change color if the samples are scrupulously maintained under controlled 40° F. conditions. However, if the samples are removed from 40° F. refrigerated storage, and exposed to an abuse condition at 80° F., the indicators will change color with one day upon being exposed to the 80° F. abuse temperature.

EXAMPLE 16

In accordance with this example, a number of fresh turkey breasts are injected with a brine solution comprising 90% water. The turkey breasts each weigh about 9.0 lbs. The turkey breasts are vacuum packaged in a commercial ethylene vinyl acetate/saran laminate film. Thereafter, the vacuum packaged turkey breasts are cooked in a high humidity oven until the internal temperature of the breasts reaches 160° F. The turkey breasts are then removed from the oven and are permitted to cool to room temperature. Thereafter, the cooled packages are placed in refrigerated storage at 40° F. In accordance with the present invention and in accordance with the method of Example 15, indicator label pouches containing the indicator solution as prepared in Example 13 are placed on the outside wrapper by means of adhesive. The indicator labels are effective to monitor the time and temperature histories of the products, exhibiting distinct color changes at times in days which varies depending on the storage treatment for that sample test product.

EXAMPLE 17

A large number of time temperature indicators in accordance with the present invention may be prepared in an automated manner as set forth hereinafter.

An indicator pouch assembly apparatus is provided including a longitudinally extending feed axis along which are arranged a reeled filter paper supply, a pair of spaced upper and lower packaging film web supplies, low temperature indicator bath solution, a paper stamping station, a seam welding station for fusing the opposing webs around a wetted indicator patch to form discrete spaced-apart indicator pouches, a perforating station whereat tear lines between adjacent label pouches are imparted to the strip, and an adhesive strip applying station, whereat a line of adhesive and contact/release sheet are applied to the outer surface of one of the web faces forming the pouches. A take up reel is also provided at the downstream end of the apparatus to provide a reeled carrier. The reeled strip of tear-off pouches may be placed in a freezer until ready for use. Thereafter, when ready for use the reeled carrier may be removed from the freezer. Individual indicator pouches may be removed from the remainder of the pouches on the reeled strip by tearing along the perforations. The indicator labels may then be placed on the exterior of the product packages by peeling the release sheet away from the adhesive strip and pressing the adhesive strip and pouch against the product packaging. Alternatively, individual indicator labels without the adhesive strip and release sheet combination, may simply be placed on the exterior of the product package in plain view, or if the product is double wrapped, in between the wrap layers.

Although the present invention has been described with reference to certain preferred embodiments, modifications or changes may be made herein by those skilled in this art without departing from the scope and spirit of this invention as defined by the appended claims.

We claim:

1. A method for making an indicator for indicating time-temperature histories in conjunction with the storage of sensitive products and compositions, comprising admixing a first specific reaction pair for generating acid, a second specific reaction pair for generating base and at least one pH sensitive dye to form an aqueous solution, said first specific reaction pair having a first substrate present in a stoichiometric excess amount over the amount of a specific substrate provide in said second specific reaction pair.

2. A method as recited in claim 1, wherein the first specific reaction pair for generating acid includes an enzyme component contributed by a microorganism source.

3. A method as recited in claim 2, wherein said microorganism is shock-treated prior to addition to the indicator solution.

4. An improved packaging for room temperature and refrigerated storage of a foodstuff including a label incorporating an indicator composition, said indicator composition being a time temperature integrating indicator comprising:
- a first specific reaction pair including an active reagent and a substrate specific to said active reagent, said first specific reaction pair being reactive to form a first reaction product, said first reaction product tending to cause the pH value to change in an acidic or a basic first direction away from neutrality;
- a second specific reaction pair including an active reagent and a substrate specific to said active reagent, said second specific reaction pair being reactive to form a second reaction product, said second reaction product tending to cause the pH value of the indicator to change in a second direction opposite said first direction and beyond neutrality;
- said first reaction product and said second reaction product in turn being reactive to form a third reaction product including a stable pH buffer which maintains the pH of the indicator at a stable value on the second direction side of neutrality until said second reaction product is no longer produced, said substrate in said first specific reaction pair being present in a stoichiometric excess amount over the amount of the substrate in said second specific reaction pair; and
- at least one pH-sensitive dye exhibiting one color for a pH in a basic pH range and a second different color in an acidic pH range, whereby said time-temperature integrating indicator exhibits a rapid and distinct color change from one to the other of said first and second colors after a pre-determined amount of time has elapsed upon exposure to relatively constant temperatures, or after a relatively shorter period of time has elapsed, upon exposure to elevated temperatures.

5. An indicator pouch for use in monitoring the time and temperature histories of an adjacent packaged food product to which said pouch is affixed, said pouch comprising a thermoplastic pouch envelope having an indicator solution-receiving cavity with a visually observable amount of a time temperature integrating indicator composition in said cavity, said indicator composition including:
- a first specific reaction pair including an active reagent and a substrate specific to said active reagent, said first specific reaction pair being reactive to form a first reaction product, said first reaction product tending to cause the pH value to change in an acidic or a basic first direction away from neutrality;
- a second specific reaction pair including an active reagent and a substrate specific to said active reagent, said second specific reaction pair being reactive to form a second reaction product, said second reaction product tending to cause the pH value of the indicator to change in a second direction opposite said first direction and beyond neutrality;
- said first reaction product and said second reaction product in turn being reactive to form a third reaction product including a stable pH buffer which maintains the pH of the indicator at a stable value on the second direction side of neutrality until said second reaction product is no longer produced, said substrate in said first specific reaction pair being present in a stoichiometric excess amount over the amount of the substrate in said second specific reaction pair; and
- at least one pH-sensitive dye exhibiting one color for a pH in a basic pH range and a second different color in an acidic pH range, whereby said time-temperature integrating indicator exhibits a rapid and distinct color change from one to the other of said first and second colors after a pre-determined amount of time has elapsed upon exposure to relatively constant temperatures, or after a relatively shorter period of time has elapsed, upon exposure to elevated temperatures.

6. An indicator pouch as defined in claim 5 further including a substrate sheet material disposed in said pouch cavity with the indicator composition.

* * * * *